United States Patent [19]

Higa et al.

[11] Patent Number: 5,043,476

[45] Date of Patent: Aug. 27, 1991

[54] DIALLYL TELLURIDE

[75] Inventors: Kelvin T. Higa; Daniel C. Harris, both of Ridgecrest, Calif.

[73] Assignee: The United States of America as represented by the Secretary of the Navy, Washington, D.C.

[21] Appl. No.: 66,442

[22] Filed: Jun. 26, 1987

[51] Int. Cl.$^5$ ............................................. C07C 395/00
[52] U.S. Cl. .................................................... 562/899
[58] Field of Search .......................... 260/550; 562/899

[56] References Cited

FOREIGN PATENT DOCUMENTS 785317 12/1980 U.S.S.R. ............................... 260/550

OTHER PUBLICATIONS

O'Brien, D. H. et al.; *Tellurium-125 and Selenium-77 NMR Shifts for Symmetric and Unsymmetric Diorganyl Chalcogenides,* Organometallics, vol. 2, No. 2, pp. 305-307, 1983.

Higa et al., J. Appl. Physics, vol. 62, p. 4929-4931 (1987).

*Primary Examiner*—John M. Ford
*Attorney, Agent, or Firm*—Stuart H. Nissim; Donald E. Lincoln; Melvin J. Sliwka

[57] ABSTRACT

The new compound diallyl telluride and other diorgano telluride compounds are prepared from alkali metal tellurides obtained by an efficient reaction between an alkali metal and tellurium in a naphthalene/tetrahydrofuran solution. The alkali metal telluride then reacts with an organo halide to form the final product which is easily isolated by filtration followed by vacuum distillation.

1 Claim, No Drawings

DIALLYL TELLURIDE

BACKGROUND OF THE INVENTION

1. Field of the Invention

The present invention is related to metal organic compounds. More particularly, the invention is related to tellurium containing organic compounds and a method for their synthesis.

2. Description of the Prior Art

Metal Organic Chemical Vapor Deposition film growth of Mercury-Cadmium-Telluride (HgCdTe) is adversely affected by the high growth temperatures of 400° C. to 425° C. which are needed to crack diethyl telluride. Problems include mercury evaporation from the film and diffusion across the interface between the film and the substrate. Ditertiarybutyl telluride has been used to deposit CdTe and HgTe films at 250° C. with excellent results. This material has been shown to work at temperatures as low as 220° C. to 230° C. However, the resulting metal films are inadequate for applications in sensitive IR detectors. Furthermore, the preparation of the tellurium source compound, ditertiarybutyl telluride, is a low yield process.

Existing processes for preparing dialkyl tellurides such as diethyl telluride use alkali metal tellurides as reactants. Current methods of preparing alkali metal tellurides employ sodium triethylborohydride or sodium borohydride. These boron containing compounds are expensive and leave trace amounts of boron in the alkali metal tellurides produced. As a result, alkali metal tellurides are expensive and contain impurities rendering them unsuitable for use in preparing electronic grade dialkyl tellurides.

Alkali metal tellurides are also prepared by reaction of an alkali metal with tellurium in liquid ammonia. The preparation requires cryogenic conditions and is hazardous because liquid ammonia is used.

SUMMARY OF THE INVENTION

A new, symmetrical dialkyl telluride compound has been synthesized and found to be useful as a tellurium source compound in the Metal Organic Chemical Vapor Deposition film growth process. The procedure for preparing diallyl telluride is new and useful for preparing other diorgano tellurides. The new compound and other diorgano telluride compounds are prepared from alkali metal tellurides obtained by an efficient reaction between an alkali metal and tellurium in a naphthalene/tetrahydrofuran solution. An alkali metal telluride then reacts with an organo halide to form a final product which is isolated by filtration followed by vacuum distillation.

An object of this invention is the new compound diallyl telluride.

Another object of this invention is an efficient, high yield process for preparing diallyl telluride and other symmetrical as well as non-symmetrical diorgano telluride compounds.

A further object of this invention is a synthesis of diorgano tellurides from alkali metal telluride compounds obtained by an efficient reaction between an alkali metal and tellurium.

DETAILED DESCRIPTION OF THE INVENTION

According to the present invention, the new composition of matter diallyl telluride is prepared in an efficient process which is also useful for preparing other symmetrical and non-symmetrical diorgano tellurides.

The new compound diallyl telluride offers many advantages over previous tellurium source compounds for Metal Organic Chemical Vapor Deposition. For example, it works well in the film growth process of mercury telluride at temperatures above 180° C., achieving the same results as previous materials at much higher temperatures. The low temperatures achieved with diallyl telluride reduce or eliminate problems associated with mercury evaporation from the film and diffusion across the interface between the film and the substrate. Additionally, diallyl telluride has a better "cracking efficiency" than the best prior materials. That is, processes using diallyl tellurides as source materials require less source material to deposit the same amount of film.

Diallyl telluride has been prepared by a process in which an alkali metal reacts with tellurium to form an alkali metal telluride. The alkali metal telluride then reacts with an alkyl halide to form a final product which is isolated by vacuum distillation. This process offers advantages over current methods of preparing dialkyl tellurides. For example, the process does not involve the use of sodium borohydride, sodium triethylborohydride or other materials which are expensive and may be left in trace amounts to render the dialkyltellurides unsuitable for use in electronic materials. Additionally, the process does not require cryogenic conditions or the use of liquid ammonia. Diallyl telluride is produced in high yields up to about 80% and the products are obtained in high purity by vacuum distillation.

An alkali metal telluride was formed under an inert atmosphere by reaction between tellurium and an alkali metal reducing mixture. The reducing mixture was prepared by adding an alkali metal to a solution of naphthalene and tetrahydrofuran. A reducing solution in which all of the alkali metal is dissolved may be used instead of a reducing mixture. Both a solution and a mixture have been found to work well in the present invention. The alkali metals lithium, sodium, and potassium have been found to work well in the reducing solutions and mixtures.

Tellurium powder or tellurium chunks were added to the reducing mixture. In the preferred embodiment, the procedure is performed as a one step or "one-pot" synthesis in which naphthalene, tetrahydrofuran, tellurium, and alkali metal are added all at once. The mixture was refluxed to drive the reaction to completion. A reflux time of at least 8 hours was found to work well for tellurium powder. Tellurium chunks require more time. Small scale reactions using about 6 grams of tellurium or less do not require heating. Stirring for about 3 days is sufficient to bring the reaction to completion. Large scale reactions using tellurium chunks often require heating for two or more days. The resulting alkali metal telluride was separated from the liquid by filtration and then dried under a vacuum to remove residual solvent. Techniques for recovering a fine powder from a solution such as centrifuging or solvent evaporation may also be used.

Dialkyl tellurides are formed under an inert atmosphere by reaction between the alkali metal telluride and an alkyl halide. A mixture of the alkali metal telluride and solvent was formed. Useful solvents include alcohols having from 1 to 5 carbon atoms and mixtures thereof, mixed solvent systems containing tetrahydrofuran and one or more of the above-stated alcohols, and mixtures of tetrahydrofuran and water. The alkali metal telluride/solvent mixture was cooled to a temperature low enough to prevent an uncontrolled exothermic reaction upon addition of an alkyl halide. Temperatures in the range from about −78° C. to about 0° C. have been found to work well. Temperatures near 0° C. are preferred.

A dialkyl telluride was formed by adding an alkyl halide to the alkali metal telluride/solvent mixture. Symmetrical dialkyl tellurides are formed by adding a single alkyl halide. Non-symmetrical dialkyl tellurides are formed by adding a mixture of alkyl halides. Organo tellurides other than alkyl tellurides are prepared by using organo halides other than alkyl halides in the synthesis. Because the reaction between alkyl halides and alkali metal tellurides is extremely exothermic, addition of an alkyl halide to the mixture must be done slowly. On a 1 mole scale, alkyl halide was added at a rate of about 1 mole per hour. After the initial exothermic reaction, the mixture may be refluxed to drive the reaction to completion. Alkyl halides having the formula RX are useful where R is an alkyl selected from the group consisting of allyl, methyl, ethyl, n-propyl, iso-propyl, n-butyl, tertiary butyl, and neopentyl; and X is a halide selected from the group consisting of chlorine, bromine and iodine.

Solid and liquid fractions of the reaction mixture were separated by filtration. However, other techniques for separating solids from liquids may be used. The crude product is contained in the liquid fraction. The solid fraction may be extracted with a solvent described above and the extract combined with the liquid fraction. Distilling the combined liquid under an inert gas removes the solvent and leaves a crude product. The temperature of the distillation should be carried out well below the decomposition temperature of the dialkyl telluride compound to be produced. As a result, it may be necessary to carry out the distillation under reduced pressure. A pure dialkyl telluride product was obtained by vacuum distillation.

In the following Examples 1 and 2, the alkali metal telluride disodium telluride ($Na_2Te$) was prepared from sodium metal and tellurium by reaction in a solution of tetrahydrofuran (THF) and naphthalene under an inert atmosphere. The examples are given to illustrate but not limit the invention:

EXAMPLE 1

Synthesis of Disodium Telluride

Under an inert atmosphere, a 1 liter flask was charged with 500 mL of dry tetrahydrofuran, 39.9 grams of sodium metal, 109.7 grams of tellurium and about 0.1 gram of naphthalene.

A water condenser was added and the system heated to reflux for about 48 hours. The water condenser was replaced with a large Schlenk frit and 1 liter flask. The $Na_2Te$ was allowed to settle for about 3 hours before separation from the reaction mixture by filtration. The solid was placed under vacuum to remove residual naphthalene. Approximately 145.9 grams of $Na_2Te$ was recovered. This represents about a 98% yield of product.

EXAMPLE 2

Synthesis of Disodium Telluride

Under an inert atmosphere, pieces of a 99.9999% pure tellurium ingot of about 1 mm in size and totalling 6.6 grams were placed in a 250 mL Schlenk flask along with 2.2 grams of sodium, 0.1 grams of naphthalene, and 20 mL of dry tetrahydrofuran.

The reaction mixture was stirred at room temperature for approximately $3\frac{1}{2}$ days. The $Na_2Te$ was separated by filtration and dried under vacuum to remove residual solvent. Approximately 7.6 grams of product was recovered giving a yield of 92%.

In the following Examples 3 and 4, diallyltelluride is prepared by the reaction between sodium telluride and allyl bromide at 0° C. in absolute ethanol under an argon atmosphere. The product is isolated via vacuum distillation in approximately 75% to 80% yield. The examples are given to illustrate but not limit the invention:

EXAMPLE 3

Synthesis of Diallyl Telluride

Under an inert atmosphere, 400 mL of freshly degassed absolute ethanol was added to approximately 62.9 grams of $Na_2Te$. The mixture was cooled to 0° C. with an ice bath. A total of 84 mL (0.97 moles) of allyl bromide was added over a period of 1 hour.

After 1 hour, the septum was replaced with a course frit attached to a 500 mL Schlenk flask. The reaction mixture was filtered to give a gray solid and a yellow filtrate.

The gray solid was extracted with 400 mL of absolute ethanol and the ethanol removed from the combined filtrate via distillation under argon at 78° C.

The product was transferred into a 250 mL round bottom flask. The liquid was distilled at 81° C. to 83° C. and at 12 torr pressure to give a white solid and an orange liquid.

The product was redistilled over the temperature range 76° C. to 78° C. at a pot temperature of 99° C. and a pressure of 12 torr. A total of 59.4 grams of product was collected giving a 78% yield. $^1H$ NMR showed only diallyl telluride.

Elemental analysis for a typical sample produced by the method of the example is as follows; Calculated: C, 34.35; H, 4.81; Te, 60.84. Found: C, 34.42; H, 5.01; Te, 59.84.

EXAMPLE 4

Synthesis of Diallyl Telluride

Under an inert atmosphere, about 250 mL of degassed absolute ethanol was added to 36.7 grams of $Na_2Te$ in a 500 mL Schlenk flask. The mixture was cooled to 0° C. with an ice bath. A total of 47.6 mL of allyl bromide was added to the stirring slurry over a period of about 20 minutes.

After 1 hour, a course filter frit having a 500 mL Schlenk flask was attached to the reaction flask. The reaction mixture was filtered to give a gray solid and a yellow filtrate.

Ethanol was removed from the filtrate via distillation under argon at a temperature within the range of about 71° C. to about 78° C.

The flask containing the residue was attached to a short-neck distillation column. A yellow liquid distilled over the temperatures from 48° C. to 54° C. This liquid was collected in a flask and attached to a vacuum distillation apparatus. The liquid was heated to 70° C. to 80° C. and the product distilled at a temperature of about 44° C. to about 45° C. and a pressure of 3.5 torr. Approximately 41.7 grams of product was collected giving a 80% yield. $^1$H NMR showed only diallyl telluride.

Modifications and variations of the present invention are possible. It should be understood that, within the scope of the appended claims, the invention may be practiced otherwise than as specifically described.

What is claimed is:

1. The composition of matter diallyl telluride.

* * * * *